(12) United States Patent
Knevels

(10) Patent No.: US 8,141,439 B2
(45) Date of Patent: Mar. 27, 2012

(54) DEVICE FOR SAMPLING METAL MELTS

(75) Inventor: Johan Knevels, Bree (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 85 days.

(21) Appl. No.: 12/619,193

(22) Filed: Nov. 16, 2009

(65) Prior Publication Data
US 2010/0122590 A1 May 20, 2010

(30) Foreign Application Priority Data

Nov. 17, 2008 (DE) .......................... 10 2008 057 797

(51) Int. Cl.
*G01N 33/20* (2006.01)
(52) U.S. Cl. .................................................. 73/864.53
(58) Field of Classification Search ................ 73/864.53
See application file for complete search history.

(56) References Cited

U.S. PATENT DOCUMENTS

| | | | |
|---|---|---|---|
| 3,321,978 A | 5/1967 | Jackson | |
| 3,656,346 A | 4/1972 | Collins | |
| 3,656,350 A | 4/1972 | Collins | |
| 3,717,034 A | 2/1973 | Dukelow et al. | |
| 3,791,219 A | 2/1974 | Falk | |
| 3,798,974 A | 3/1974 | Boron | |
| 3,820,380 A | 6/1974 | Miller et al. | |
| 3,877,309 A | 4/1975 | Hance | |
| 4,002,072 A | 1/1977 | Collins | |
| 4,007,641 A | 2/1977 | Kelsey | |
| 4,059,996 A | 11/1977 | Cure | |
| 4,089,223 A | 5/1978 | Collins | |
| 4,179,931 A | 12/1979 | Moriya | |
| 4,291,585 A | 9/1981 | Kolb et al. | |
| 4,338,841 A | 7/1982 | Collins | |
| 4,338,842 A | 7/1982 | Collins | |
| 4,361,053 A | 11/1982 | Jones et al. | |
| 4,503,716 A | 3/1985 | Wuensch | |
| 4,515,485 A * | 5/1985 | Cassidy et al. | 374/157 |
| 4,932,271 A | 6/1990 | Haughton | |
| 4,941,364 A | 7/1990 | Haughton | |

(Continued)

FOREIGN PATENT DOCUMENTS

DE 7405180 U 6/1974

(Continued)

OTHER PUBLICATIONS

EP Search Report issued May 9, 2011 in EP Application No. 09014105; Written Opinion.

(Continued)

Primary Examiner — Hezron E Williams
Assistant Examiner — Gregory J Redmann
(74) Attorney, Agent, or Firm — Panitch Schwarze Belisario & Nadel LLP

(57) ABSTRACT

A device is provided for sampling metal melts, in particular molten iron and molten cast iron, with a sample chamber having an inlet opening and tellurium arranged in the sample chamber. The sample chamber contains 0.01 to 0.05 g/cm$^3$ tellurium based on the volume of the sample chamber and the tellurium is in powder form having an average particle size of at most 150 μm. Additionally or alternatively, the tellurium is in powder form having an average particle size of at least 150 μm and a specific surface area of 0.03 to 0.1 m$^2$/g.

5 Claims, 3 Drawing Sheets

U.S. PATENT DOCUMENTS

| | | | |
|---|---|---|---|
| 5,057,149 A * | 10/1991 | Conti et al. | 75/377 |
| 5,151,243 A | 9/1992 | Auer et al. | |
| 5,537,881 A | 7/1996 | White | |
| 5,948,350 A | 9/1999 | Falk | |
| 5,979,253 A | 11/1999 | Knevels et al. | |
| 6,155,122 A | 12/2000 | Junker et al. | |
| 6,370,973 B1 | 4/2002 | Wunsch et al. | |
| 6,581,482 B2 | 6/2003 | Cappa et al. | |
| 6,811,742 B2 | 11/2004 | Knevels | |
| 6,883,392 B2 | 4/2005 | Knevels et al. | |
| 2001/0020397 A1 | 9/2001 | Cappa et al. | |
| 2003/0062661 A1 | 4/2003 | Knevels | |
| 2005/0132823 A1 | 6/2005 | Knevels et al. | |

FOREIGN PATENT DOCUMENTS

| | | |
|---|---|---|
| DE | 26 46 539 A1 | 10/1977 |
| DE | 2714636 A1 | 10/1977 |
| DE | 2840745 B2 | 3/1980 |
| DE | 3402818 A1 | 8/1985 |
| DE | 8910869 U1 | 10/1989 |
| DE | 4009167 A1 | 9/1991 |
| DE | 19752743 A1 | 6/1999 |
| DE | 19916234 A1 | 9/2000 |
| DE | 10049253 A1 | 9/2001 |
| EP | 0 436 063 B1 | 7/1991 |
| EP | 0447613 A2 | 9/1991 |
| EP | 1126036 A1 | 8/2001 |
| FR | 2026247 A1 | 9/1970 |
| FR | 2171627 A5 | 9/1973 |
| GB | 883833 A | 12/1961 |
| GB | 981357 A1 | 1/1965 |
| GB | 1235800 A | 6/1971 |
| GB | 2335738 A | 9/1999 |
| JP | 241871972 | 11/1972 |
| JP | 08321785 | 5/1985 |
| JP | 61077761 A | 4/1986 |
| JP | 61271452 A | 12/1986 |
| JP | 05273197 A | 10/1993 |
| JP | 06265539 A | 9/1994 |
| JP | 07306196 A | 11/1995 |
| JP | 11304669 A | 11/1999 |
| SU | 601595 A1 | 4/1978 |
| SU | 1411612 A1 | 7/1988 |
| WO | 0073765 A1 | 12/2000 |

OTHER PUBLICATIONS

Office Action issued on Jun. 21, 2004 in U.S. Appl. No. 10/340,416.
European Search Report issued on Jun. 25, 2004 in European Application No. EP 02 02 7794.
Office Action issued on Mar. 11, 2010 in German Application No. 10 2008 057 797.9-52.
Office Action issued on Feb. 1, 2002 in German Application No. 101 48 112.8-52.
Office Action issued on Apr. 6, 2004 in U.S. Appl. No. 10/256,898.
Office Action issued on Oct. 6, 2003 in U.S. Appl. No. 10/256,898.
Office Action issued on Aug. 22, 2002 in U.S. Appl. No. 09/788,224.
Office Action issued on Jan. 16, 2001 in German Application No. 100 49 253.3-52.
Office Action issued on Jun. 22, 2001 in European Application No. EP 01 10 3404.
Office Action issued on May 14, 2002 in German Application No. DE 102 01 0234.4-52 (with partial English translation).
EP Search Report issued Sep. 19, 2005 in EP Appln. No. EPO4 02 5718.
Office Action issued Nov. 16, 2006 in U.S. Appl. No. 11/012,473.
Office Action issued Mar. 14, 2007 in U.S. Appl. No. 11/012,473.
Office Action issued Jan. 13, 2009 in U.S. Appl. No. 11/012,473.
Office Action issued Aug. 11, 2009 in U.S. Appl. No. 11/012,473.
Office Action issued Jan. 27, 2010 in U.S. Appl. No. 11/012,473.
Office Action issued Apr. 6, 2004 in U.S. Appl. No. 10/256,898.
Office Action issued Oct. 6, 2003 in U.S. Appl. No. 10/256,898.
Office Action issued Jun. 21, 2004 in U.S. Appl. No. 10/340,416.

* cited by examiner

DEVICE FOR SAMPLING METAL MELTS

BACKGROUND OF THE INVENTION

The invention relates to a device for sampling metal melts, in particular molten iron and molten cast iron, with a sample chamber having an inlet opening, wherein tellurium is arranged in the sample chamber.

From German published patent application DE 2646539 A1 a vessel is known for determining the solidification temperature of metal melts in which a layer of bound tellurium is arranged on the vessel floor. This mixture with a refractory material and a hydrogen-generating material should cause a delayed release of the tellurium. The tellurium itself should then improve the so-called white solidification (chill structure) of the melt poured into the vessel. From European Patent EP 436063 B1 it is known to arrange a mixture with tellurium in the sealing cap of the inlet opening of a sampler for molten metal. This mixture is flushed into the sample chamber with the incoming molten metal when the sealing cap is destroyed. A similar device is disclosed in U.S. Pat. No. 5,948,350.

BRIEF SUMMARY OF THE INVENTION

The invention is based on the object of making available sampling devices in which metal samples can be obtained with optimal white solidification.

The object is achieved by embodiments of the present invention described and claimed in the following. Surprisingly, it has been shown that, contrary to the teaching of the prior art, the best results are obtained when pure tellurium is distributed homogeneously in the sample.

This is achieved with the devices according to embodiments of the invention, wherein the sample chamber contains 0.01 to 0.05 g/cm$^3$ tellurium, based on the volume of the sample chamber, and wherein the tellurium is in the form of a powder having an average particle size of at most 150 μm or wherein the tellurium is in the form of a powder having an average particle size of at most 150 μm and a specific surface area of 0.03 to 0.1 m$^2$/g.

Preferably, the sample chamber contains 0.015 to 0.025 g/cm$^3$ tellurium. It is further expedient that the specific surface area be 0.06 to 0.07 m$^2$/g.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
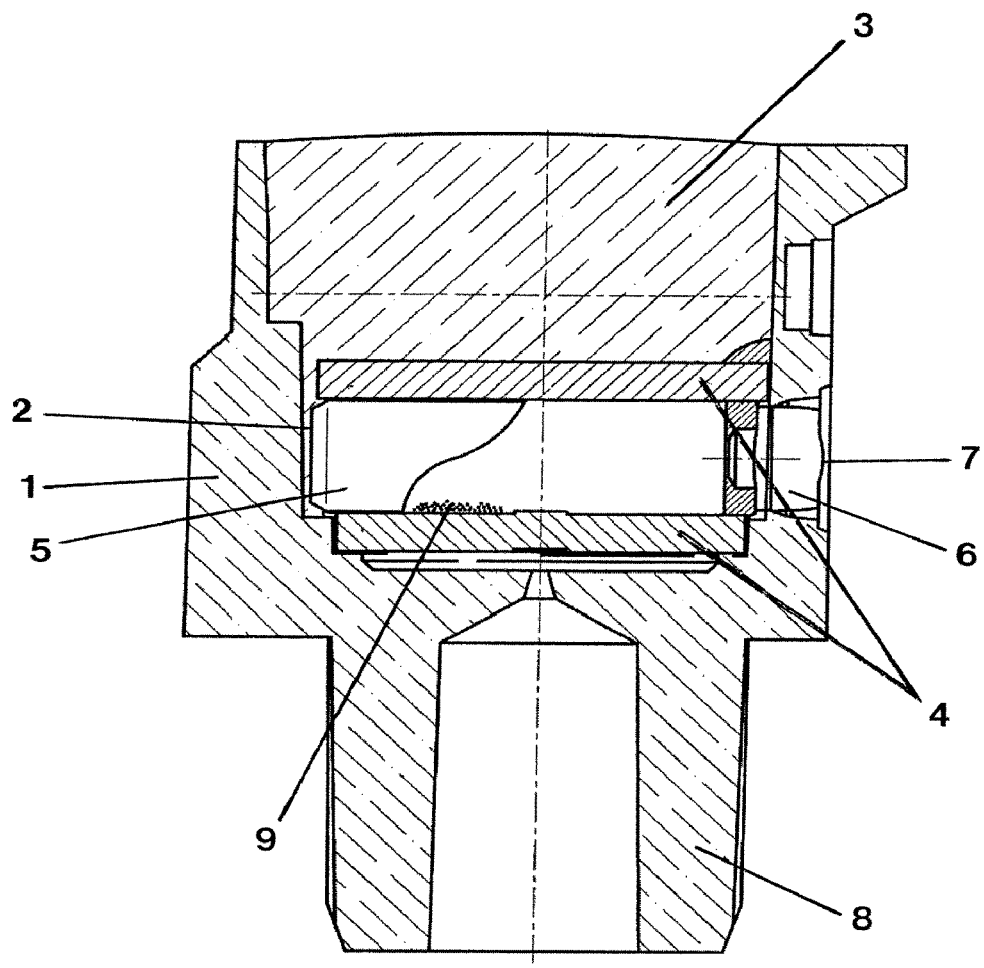
FIG. 1 is a longitudinal cross section through a sampler according to an embodiment of the invention.

A sampler according to the invention has a body 1 made of a molding sand, in which a sample chamber 2 is arranged in an opening. The opening is closed on the immersion side of the sampler with a sand body 3. The sample chamber 2 has a circular outline with a diameter of approximately 35 mm and a height of approximately 10 mm. The base surfaces are each formed of metal plates 4, and the lateral surface lying in-between is made of a ceramic ring 5.

On the right side of FIG. 1 the inlet opening 6 is shown, which is bounded by a quartz tube. The quartz tube is closed with a protective cap 7.

The body 1 has a connection port 8 for a conventional carrier tube. The carrier tube could be formed of paperboard.

In the sample chamber 2 approximately 0.2 g tellurium powder 9 is arranged, which corresponds to approximately 0.02 g/cm$^3$ based on the chamber volume. The powder was produced by grinding and has an average particle size of less than 100 μm and a specific surface area of approximately 0.065 m$^2$/g. The average particle size was determined by laser diffraction using a Sympatec particle analyzer from Sympatec GmbH. The specific surface area of the powder was determined by gas absorption laboratory analysis using the B.E.T. method. It will be understood that the values given herein for these properties of the powder are based on these methods of determination.

Figure 2:
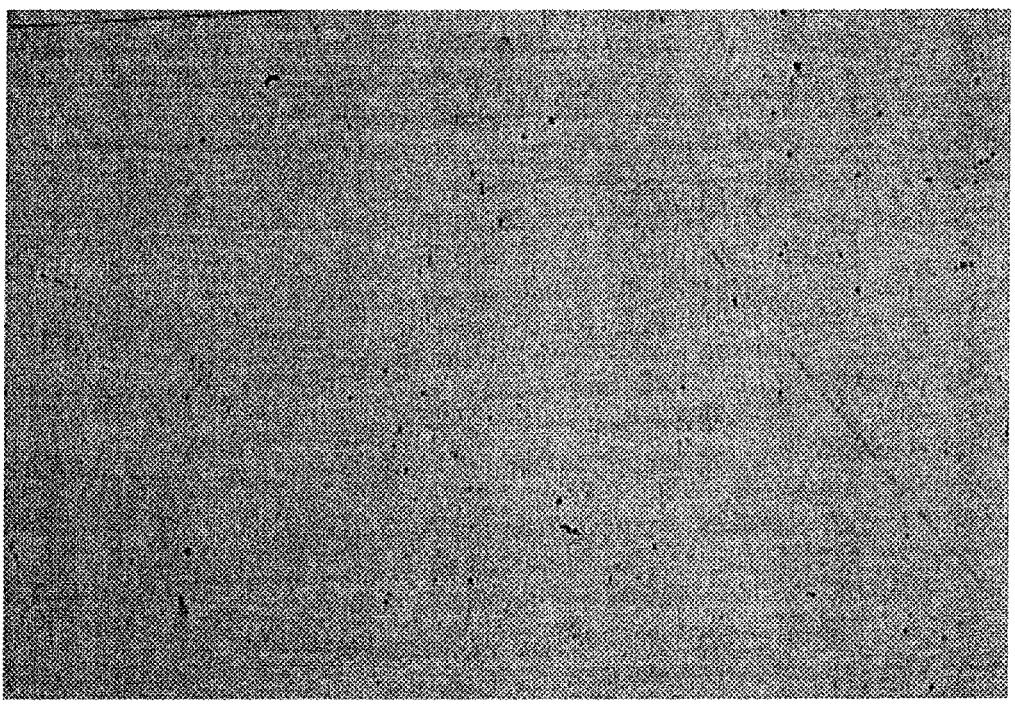
FIG. 2 is a polished section of a white solidified sample.
Figure 3:
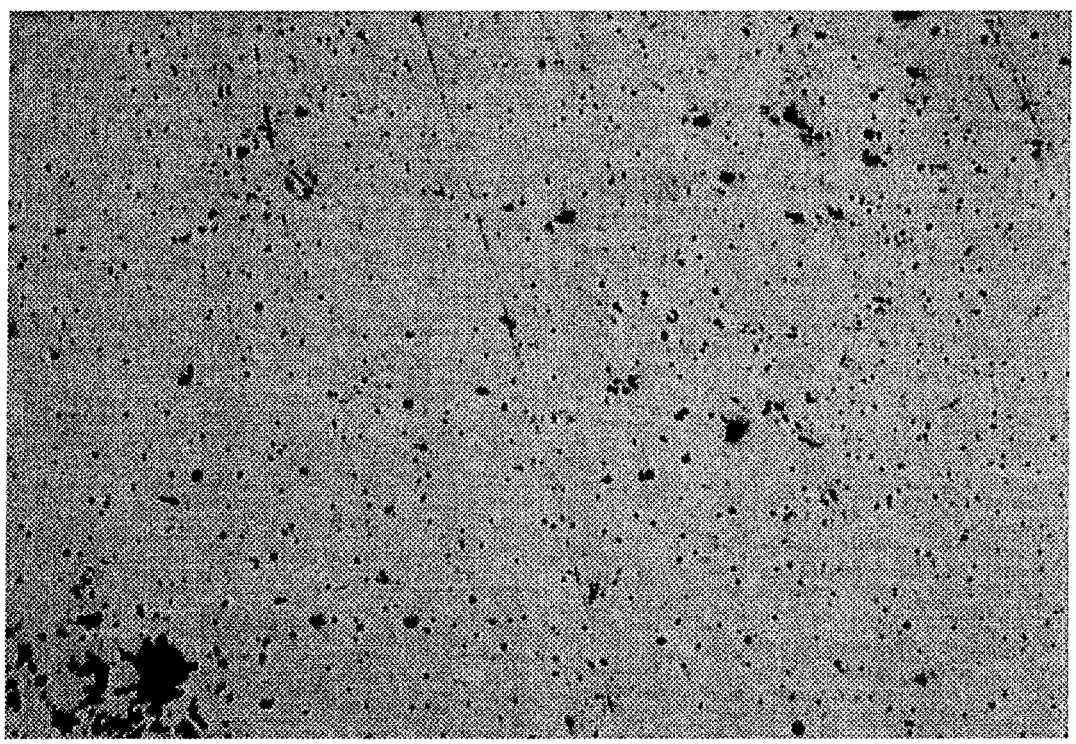
FIG. 3 is a polished section of a conventional sample, without tellurium additive.

Since the specific surface area and volume or mass are not in a direct relationship with each other, the fulfillment of even one of the conditions described above already leads to the advantages according to the invention, which are apparently realized because the powder surprisingly mixes homogeneously with the molten metal when the melt enters into the sample chamber. This leads to the desired white solidification shown in FIG. 2. In contrast, the non-homogeneous solidification shown in FIG. 3 is produced without tellurium.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device for sampling metal melts, in particular molten iron and molten cast iron, the device comprising a sample chamber having an inlet opening and tellurium arranged in the sample chamber, wherein the sample chamber contains 0.01 to 0.05 g/cm$^3$ tellurium based on a volume of the sample chamber, and wherein the tellurium is in powder form having an average particle size of at most 150 μm.

2. The device according to claim 1, wherein the sample chamber contains 0.015 to 0.025 g/cm$^3$ tellurium.

3. A device for sampling metal melts, in particular molten iron and molten cast iron, the device comprising a sample chamber having an inlet opening and tellurium arranged in the sample chamber, wherein the tellurium is in powder form having an average particle size of at most 150 μm and a B.E.T. specific surface area of 0.03 to 0.1 m$^2$/g.

4. The device according to claim 3, wherein the B.E.T. specific surface area is 0.06 to 0.07 m$^2$/g.

5. The device according to claim 1, wherein the tellurium is arranged within an interior of the sample chamber when the sample chamber contains metal melts and when the sample chamber does not contain metal melts.

* * * * *